United States Patent [19]

Denzel et al.

[11] 3,953,461

[45] Apr. 27, 1976

[54] AMINO DERIVATIVES OF THIAZOLO[5,4-b]PYRIDINE-6-CARBOXYLIC ACIDS AND ESTERS

[75] Inventors: Theodor Denzel, Regensburg; Hans Hoehn, Tegernheim, both of Germany

[73] Assignee: E. R. Squibb & Sons, Inc., Princeton, N.J.

[22] Filed: Mar. 5, 1975

[21] Appl. No.: 555,512

[52] U.S. Cl. ................. 260/294.8 C; 260/294.8 G; 424/266
[51] Int. Cl.² ........................................ C07D 213/55
[58] Field of Search ............................ 260/294.8 C

[56] References Cited
UNITED STATES PATENTS 3,887,570  6/1975  Denzel et al. .............. 260/294.8 B

*Primary Examiner*—Alan L. Rotman
*Attorney, Agent, or Firm*—Lawrence S. Levinson; Merle J. Smith

[57] ABSTRACT

The new derivatives of thiazolo[5,4-b]pyridine-6-carboxylic acids, esters and their salts which have the general formula

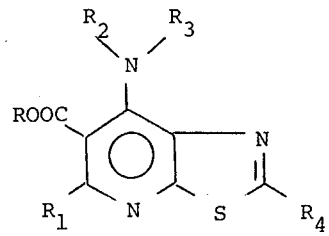

are useful as central nervous system depressants and antiinflammatory agents.

9 Claims, No Drawings

AMINO DERIVATIVES OF THIAZOLO[5,4-B]PYRIDINE-6-CARBOXYLIC ACIDS AND ESTERS

SUMMARY OF THE INVENTION

The invention relates to new amino derivatives of thiazolo[5,4-b]pyridine-6-carboxylic acids and esters and salts thereof, having the general formula

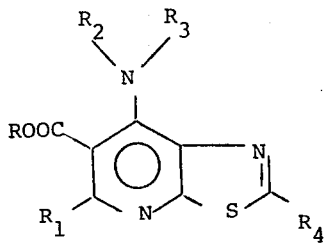
(I)

The symbols have the following meaning in formula I and throughout this specification:

The basic nitrogen group

is an acylic amino moiety, wherein $R_2$ and $R_3$ each is hydrogen, lower alkyl, phenyl or di(lower alkyl)amino-lower alkyl, preferably only one of the last two is present in the basic nitrogen group.

R, $R_1$ and $R_4$ each is hydrogen or lower alkyl.

The lower alkyl groups in any of the foregoing radicals include straight or branched chain hydrocarbon groups containing 1 to 7 carbon atoms. Examples of the groups contemplated are methyl, ethyl, propyl, isopropyl, etc. Lower alkyl groups of 1 to 4 carbon atoms are preferred, especially the 1 to 2 carbon members of this group.

Preferred embodiments of this invention are as follows:

R is hydrogen or lower alkyl of 1 to 4 carbon atoms, especially ethyl.

$R_1$ is hydrogen or lower alkyl of 1 to 4 carbon atoms, especially methyl.

$R_2$ and $R_3$ each is hydrogen, lower alkyl of 1 to 4 carbon atoms, especially butyl and $R_3$ is di(lower alkyl)amino-lower alkyl, especially dimethylaminopropyl, when $R_2$ is hydrogen.

$R_4$ is hydrogen or lower alkyl of 1 to 4 carbon atoms, especially hydrogen and methyl.

DETAILED DESCRIPTION

The new compounds of formula I are formed by the following series of reactions. The symbols in the structural formulas have the same meaning as previously described.

A 4,6-dihydroxy-pyridine-3-carboxylic acid ester of the formula

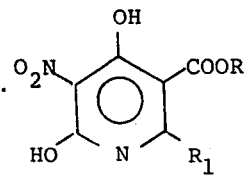
(II)

[produced analogous to the procedure described in Chem.Ber. 99, 244 (1966)] wherein R is lower alkyl, is made to react with an inorganic acid chloride like phosphorus oxychloride producing a compound of the formula

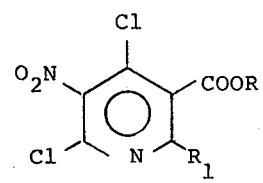
(III)

with two chloride atoms in the 4- and 6-positions of the molecule. This compound is now treated with an amine of the formula

(IV)

in the presence of a base, e.g., an alkylamine like triethylamine, forming a compound of the formula

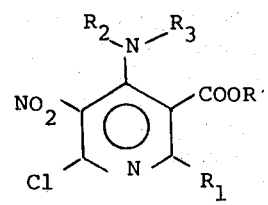
(V)

Reaction of the compound of formula V with an alkali metal sulfide like sodium sulfide, produces a compound of the formula

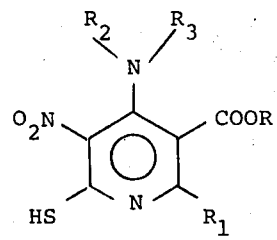
(VI)

with a mercapto group in the 6-position. This compound is now reduced by means of a metal pair like zinc in acetic acid. This reaction results in the formation of a compound of the formula

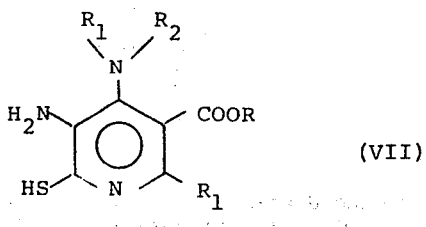

Compounds of formula I are now produced by reaction of the compound of formula VII with the appropriate orthocarbonic acid ester of the formula $$R_4-C(OC_2H_5)_3 \qquad (VIII)$$

or with the corresponding carbonic acid of the formula $$R_4-COOH \qquad (IX)$$

The esters are converted to the acid, i.e., wherein R is hydrogen, with a dilute alkali metal hydroxide like sodium hydroxide.

The compounds of formula I form salts which are also part of this invention. They form acid addition salts by reaction with a variety of inorganic and organic acids providing acid addition salts including, for example, hydrohalides (especially the hydrochloride and hydrobromide), sulfate, nitrate, phosphate, oxalate, tartrate, malate, citrate, picrate, acetate, ascorbate, succinate, arylsulfonates like benzenesulfonate, toluenesulfonate, alkanesulfonates like methanesulfonate, cyclohexanesulfamate, etc. The acid addition salts frequently provide a convenient means for isolating the product, e.g., by forming and precipitating the salt in an appropriate menstruum in which the salt is insoluble, then after separation of the salt, neutralizing with an aqueous base such as barium hydroxide or sodium hydroxide, to obtain the free base of formula I. Other salts may then be formed from the free base by reaction with an equivalent of acid.

The compounds of formula I also form basic salts with strong bases, e.g., upon vigorous treatment with bases like alkali metal hydroxides or alkaline earth metal hydroxides the corresponding metal salt is formed. R in this instance is then alkali metal or alkaline earth metal. The physiologically acceptable salts are preferred.

The new compounds of this invention are central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable acid addition salt or metal salt thereof, is administered orally or parenterally in a conventional dosage form such as tablet, capsule, injectable or the like. A single dose, or preferably 2 to 4 divided daily doses, provided on a basis of about 1 to 50 mg/kg/day, preferably about 2 to 15 mg/kg/day, is appropriate. These can be conventionally formulated in an oral or parenteral dosage form by compounding about 10 to 250 mg. per unit of dosage with conventional vehicle, excipient, binder, preservative, stabilizer, flavor or the like, and if necessary sterilized, all as called for by accepted pharmaceutical practice.

The compounds of this invention are also useful as antiinflammatory agents and are effective in the prevention and inhibition of granuloma tissue formation in warm blooded animals, for example, in a manner similar to indomethacin. For example, about 150 mg/kg/day is effective in reduced paw swelling in rats. They can be used to decrease joint swelling tenderness, pain and stiffness, in various mammalian species, e.g., in conditions such as rheumatoid arthritis. A compound of this invention or a physiologically acceptable salt of the character described above is compounded according to accepted pharmaceutical practice in oral dosage forms such as tablets, capsules, elixirs or powders for administration of about 100 mg. to 2 gm. per day, preferably 100 mg. to 1 gm. per day, in two to four divided doses.

The following examples constitute preferred embodiments and also illustrate how these and other members of this group are produced. Simple variation of the reactants and substitution in the reaction sequences described below, readily yield other compounds within the scope of the invention. All temperatures are in degrees centigrade.

EXAMPLE 1

7-(Butylamino)-5-methylthiazolo[5,4-b]pyridine-6-carboxylic acid ethyl ester a. 4,6-Dichloro-2-methyl-5-nitropyridine-3-carboxylic acid ethyl ester 242 g. of 4,6-dihydroxy-2-methyl-5-nitropyridine-3-carboxylic acid ethyl ester (1 Mol.) are heated at 80° with 500 ml. of phosphorus oxychloride for 60 hours. After this time, the excess phosphorus oxychloride is removed in vacuo and the black residue is decomposed by pouring into ice water. The precipitate, 4,6-dichloro-2-methyl-5-nitropyridine-3-carboxylic acid, ethyl ester, is filtered off and recrystallized from petroleum ether using charcoal, yield 195 g. (70%), m.p. 45°–46° b. 4-Butylamino-6-chloro-2-methyl-5-nitropyridine-3-carboxylic acid, ethyl ester 139.5 g. of 4,6-dichloro-2-methyl-5-nitropyridine-3-carboxylic acid, ethyl ester (0.5 Mol.) are dissolved in about 500 ml. of methanol. 60 g. of triethylamine are added and the solution is heated at reflux temperature. At this point, 36.5 g. of n-butylamine are added dropwise. After the addition is completed, the heating is continued for ten minutes. The solvent is then removed in vacuo and 500 ml. of ethyl acetate are added to the residue. The triethylamine hydrochloride is filtered off and the solvent evaporated. The resulting yellow oil is crystallized with 300 ml. of methanol to give 4-butylamino-6-chloro-2-methyl-5-nitropyridine-3-carboxylic acid, ethyl ester, yield 110 g. (70%), m.p. 33°–35° (methanol).

c. 4-Butylamino-6-mercapto-2-methyl-5-nitropyridine-3-carboxylic acid, ethyl ester 31.5 g. of 4-butylamino-6-chloro-2-methyl-5-nitropyridine-3-carboxylic acid ethyl ester (0.1 Mol.) are dissolved in 100 ml. of alcohol. 14.8 g. of sodium sulfide monohydrate and about 2 ml. of water are added and the mixture is stirred for one hour without cooling. The precipitated 4-butylamino-6-mercapto-2-methyl-5-nitropyridine-3-carboxylic acid, ethyl ester is filtered off, yield 27.5 g. (88%), m.p. 140°–142° (ethanol).

d. 5-Amino-4-butylamino-6-mercapto-2-methylpyridine-3-carboxylic acid, ethyl ester 6.2 g. of 4-butylamino-6-mercapto-2-methyl-5-nitropyridine-3-carboxylic acid, ethyl ester (0.02 Mol.) are dissolved in 25 ml. of acetic acid at reflux temperature with stirring. Zinc dust is added cautiously in small portions until the solvent is colorless. The inorganic precipitate is then filtered off, the solvent is removed and the residue is dissolved in 10 ml. of methanol. The product 5-amino-4-butylamino-6-mercapto-2-methylpyridine-3-carboxylic acid, ethyl ester precipitates after the addition of aqueous ammonia, yield 3.6 g. (64%), m.p. 103°–105° (ethyl acetate).

e. 7-(Butylamino)-5-methylthiazolo[4,5-b]pyridine-6-carboxylic acid, ethyl ester 2.8 g. of 5-amino-4-butylamino-6-mercapto-2-methylpyridine-3-carboxylic acid, ethyl ester and 10 ml. of orthoformic acid triethyl ester are refluxed for 24 hours. After this time, the excess ortho ester is removed in vacuo and the residue is treated with 20 ml. of diethyl ether. The insoluble compound is filtered off and the filtrate is cooled to about −20°. 7-(Butylamino)-5-methylthiazolo[5,4-b]pyridine-6-carboxylic acid, ethyl ester crystallizes and is filtered off, yield 2.2 g. (76%), m.p. 57°–60° (petroleum ether).

The hydrochloride is formed by adding to a solution of the above product an alcoholic solution of hydrogen chloride.

EXAMPLE 2

7-(Butylamino)-5-methylthiazolo[5,4-b]pyridine-6-carboxylic acid, sodium salt 2.9 g. of 7-(butylamino)-5-methylthiazolo[5,4-b]pyridine-6-carboxylic acid, ethyl ester are heated in alcohol together with 1 g. of sodium hydroxide at 70° for 20 hours. The solvent is removed in vacuo and the residue is dissolved in about 3 ml. of methanol and precipitated by the addition of ether to obtain 7-(butylamino)-5-methylthiazolo[5,4-b]pyridine-6-carboxylic acid, sodium salt, yield 2.2 g. (81%).

EXAMPLE 3

7-[[3-(Dimethylamino)propyl]amino]-2,5-dimethylthiazolo[5,4-b]pyridine-6-carboxylic acid, ethyl ester a. 4-[[3-(Dimethylamino)propyl]amino]-6-chloro-2-methyl-5-nitropyridine-3-carboxylic acid, ethyl ester 139 g. of 4,6-dichloro-2-methyl-5-nitropyridine-3-carboxylic acid, ethyl ester (0.5 Mol.) are dissolved in about 500 ml. of methanol. 60 g. of triethylamine are added and the solution is heated at reflux temperature. At this point, 50.1 g. of [3-(dimethylamino)propyl]amine are added dropwise. After the addition is completed, heating is continued for 10 minutes. The solvent is removed in vacuo and the residue is suspended with 200 ml. of water. The aqueous mixture is made alkaline with 10% sodium hydroxide solution and extracted three times with 200 ml. portions of ethyl acetate. The organic layer is dried over calcium chloride, evaporated to dryness and crystallized with petroleum ether to obtain 4-[[3-(dimethylamino)propyl]amino]-6-chloro-2-methyl-5-nitropyridine-3-carboxylic acid, ethyl ester, yield 102 g. (59%), m.p. 20°.

b. 4-[[3-(Dimethylamino)propyl]amino]-6-mercapto-2-methyl-5-nitropyridine-3-carboxylic acid, ethyl ester 34.5 g. of 4-[[3-(dimethylamino)propyl]amino]-6-chloro-2-methyl-5-nitropyridine-3-carboxylic acid, ethyl ester are dissolved in 100 ml. of ethanol. 15 g. of sodium sulfide in 10 ml. of water are added and the mixture is stirred without cooling for 1 hour. After this time, the precipitated 4-[[3-(dimethylamino)propyl]amino]-6-mercapto-2-methyl-5-nitropyridine-3-carboxylic acid, ethyl ester is filtered off and recrystallized from methanol, yield 18 g. (53%), m.p. 131°–132°.

c. 5-Amino-4-[[3-(dimethylamino)propyl]amino]-6-mercapto-2-methylpyridine-3-carboxylic acid, ethyl ester 6.8 g. of 4-[[3-(dimethylamino)propyl]amino]-6-mercapto-2-methylpyridine-3-carboxylic acid, ethyl ester are dissolved in 50 ml. of acetic acid and held at reflux temperature. Zinc dust is added until the solution is colorless. The inorganic precipitate is filtered off, the solvent removed and the residue dissolved in about 10 ml. of methanol. The 5-amino-4-[[3-(dimethylamino)propyl]amino]-6-mercapto-2-methylpyridine-3-carboxylic acid, ethyl ester crystallizes on addition of aqueous ammonia, yield 4.1 g. (66%), m.p. 110°–112° (ethyl acetate).

d. 7-[[3-(Dimethylamino)propyl]amino]-2,5-dimethylthiazolo[5,4-b]pyridine-6-carboxylic acid, ethyl ester 3.1 g. of 5-amino-4-[[3-(dimethylamino)propyl amino]-6-mercapto-2-methylpyridine-3-carboxylic acid, ethyl ester and 5 ml. of orthoacetic acid triethyl ester are refluxed for 15 hours. The excess ortho ester is distilled off and the residue is dissolved in 30 ml. of ether. The insoluble compound is filtered off and the filtrate cooled to about −40° 7-[[3-(Dimethylamino)propyl]amino]-2,5-dimethylthiazolo[5,4-b]pyridine-6-carboxylic acid, ethyl ester crystallizes, yield 2.1 g. (68%), m.p. 53°–54° (petroleum ether).

EXAMPLE 4

7-sec.Butylamino-5-methylthiazolo[5,4-b]pyridine-6-carboxylic acid, ethyl ester a. 4-sec. Butylamino-6-chloro-2-methyl-5-nitropyridine-3-carboxylic acid, ethyl ester By replacing the n-butylamine with sec. butylamine in the procedure of Example 1b, 4-sec.butylamino-6-chloro-2-methyl-5-nitropyridine-3-carboxylic acid, ethyl ester is obtained, yield 68%, m.p. 31°–32° (methanol).

b. 4-sec.Butylamino-6-mercapto-2-methyl-5-nitropyridine-3-carboxylic acid, ethyl ester By replacing the 4-butylamino-6-mercapto-2-methyl-5-nitropyridine-3-carboxylic acid, ethyl ester with 4-sec. butylamino-6-chloro-2-methyl-5-nitropyridine-3-carboxylic acid, ethyl ester in the procedure of Example 1c, 4-sec.butylamino-6-mercapto-2-methyl-5-nitropyridine-3-carboxylic acid, ethyl ester is obtained, yield 82%, m.p. 156°–157° (methanol).

c. 5-Amino-4-sec.butylamino-6-mercapto-2-methylpyridine-3-carboxylic acid, ethyl ester 6.2 g. of 4-sec. butylamino-6-mercapto-2-methyl-5-nitropyridine-3-carboxylic acid, ethyl ester are dissolved in 50 ml. of acetic acid. Iron dust is added carefully at relufx temperature until the mixture is colorless. The excess iron is filtered off and the filtrate is evaporated to dryness. The oily residue is dissolved in 10 ml. of methanol and precipitated by the addition of aqueous ammonia to obtain 5-amino-4-sec.butylamino- 6-mercapto-2-methylpyridine-3-carboxylic acid, ethyl ester, yield 3 g. (53%), m. p. 88°–89° (ethyl acetate).

d. 7-sec.Butylamino-5-methylthiazolo[5,4-b]pyridine-6-carboxylic acid, ethyl ester 2.8 g. of 5-amino-4-sec.butylamino-6-mercapto-2-methylpyridine-3-carboxylic acid, ethyl ester are refluxed in 10 ml. of formic acid for 12 hours. After this time, the excess acid is removed in vacuo and the residue is dissolved in 10 ml. of water. The aqueous solution is made alkaline with sodium hydroxide and extracted twice, each time with 10 ml. of ether. The ether layer is collected, dried over calcium chloride and evaporated to dryness. The residue, 7-sec.butylamino-5-methylthiazolo[5,4-b]pyridine-6-carboxylic acid, ethyl ester is distilled in vacuo, b. $p_{.0.01}$ 180°–185°, yield 1.8 g. (62%).

EXAMPLE 5

7-Butylamino-2,5-dimethylthiazolo[5,4-b]pyridine-6-carboxylic acid, ethyl ester

By replacing the orthoformic acid triethyl ester with orthoacetic acid triethyl ester in the procedure of Example 1e, 7-butylamino-2,5-dimethylthiazolo[5,4-b]pyridine-6-carboxylic acid, ethyl ester is obtained, yield 71%, m.p. 53°–54° (petroleum ether).

EXAMPLE 6

7-(Isopropyl)amino-5-methylthiazolo[5,4-b]pyridine-6-carboxylic acid, ethyl ester By replacing the butylamine with isopropylamine in the procedure of Example 1b, and this compound is processed according to Examples 1b–e, 7-(isopropyl)amino-5-methylthiazolo[5,4-b]pyridine-6-carboxylic acid, ethyl ester is obtained, m.p. 48°–50°.

EXAMPLE 7

7-(Ethyl)amino-5-methylthiazolo[5,4-b]pyridine-6-carboxylic acid, ethyl ester

By replacing the butylamine with ethylamine in the procedure in Example 1b, and the compound processed as described in Examples 1b–e, 7-(ethyl)amino-5-methylthiazolo[5,4-b]pyridine-6-carboxylic acid, ethyl ester is obtained, m.p. 53°–54°.

EXAMPLE 8

7-[[3-(Dimethylamino)propyl]amino]-5-methylthiazolo[5,4-b]pyridine-6-carboxylic acid, ethyl ester By replacing the orthoacetic acid triethyl ester in Example 3 d with orthoformic acid triethyl ester, 7-[[3-(dimethylamino)propyl]amino]-5-methylthiazolo[5,4-b]pyridine-6-carboxylic acid, ethyl ester is formed, $b.p._{0.01}$ 190°–195°.

EXAMPLE 9

7-Amino-5-methylthiazolo[5,4-b]pyridine-6-carboxylic acid, ethyl ester a. 4-tert.Butylamino-6-chloro-2-methyl-5-nitropyridine-3-carboxylic acid, ethyl ester By replacing n-butylamine in the procedure of Example 1b with tert.butylamine, 4-tert.butylamino-6-chloro-2-methyl-5-nitropyridine-3-carboxylic acid, ethyl ester is formed, m.p. 35°–36°, yield 68%.

b. 4-Amino-6-chloro-2-methyl-5-nitropyridine-3-carboxylic acid, ethyl ester 3.2 g. of 4-tert.butylamino-6-chloro-2-methyl-5-nitropyridine-3-carboxylic acid, ethyl ester is heated at 240° for 10 minutes. After cooling, the resulting 4-amino-6-chloro-2-methyl-5-nitropyridine-3-carboxylic acid, ethyl ester is recrystallized from methanol, m.p. 73°–75° (75%).

c. 7-Amino-5-methylthiazolo[5,4-b]pyridine-6-carboxylic acid, ethyl ester

By treating 4-amino-6-chloro-2-methyl-5-nitropyridine-3-carboxylic acid ethyl ester as described in Example 1c–e, 7-amino-5-methylthiazolo[5,4-b]pyridine-6-carboxylic acid ethyl ester is formed, m.p. 118°–119°.

d. 7-Amino-5-methylthiazolo[5,4-b]pyridine-6-carboxylic acid

By treating 7-amino-5-methylthiazolo[5,4-b]-6-carboxylic acid, ethyl ester with barium hydroxide, 7-amino-5-methylthiazolo[5,4-b]pyridine-6-carboxylic acid is obtained.

The following additional products are produced by the procedure of Examples 1, 2 and 3 by substituting the appropriately substituted pyrdinecarboxylic acid ($R$, $R_1$), amine ($R_2$, $R_3$) and carbonic acid ($R_4$):

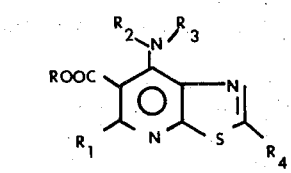

| Example | R | $R_1$ | $N{<}^{R_2}_{R_3}$ | $R_4$ | Salt |
|---|---|---|---|---|---|
| 10 | $CH_3$ | $CH_3$ | $N(C_2H_5)_2$ | H | HCl |
| 11 | $C_2H_5$ | $CH_3$ | $NH_2$ | $C_2H_5$ | |
| 12 | $C_2H_5$ | $C_2H_5$ | $N(CH_3)_2$ | H | |
| 13 | H | H | $NH(C_4H_9)$ | H | HBr |
| 14 | $C_2H_5$ | H | $N(CH_3)_2$ | $CH_3$ | |
| 15 | $C_3H_7$ | H | $NHC_4H_9$ | H | |
| 16 | $C_2H_5$ | H | NH–C₆H₅ (phenyl) | H | |
| 17 | $C_2H_5$ | $CH_3$ | NH–C₆H₅ (phenyl) | $CH_3$ | |
| 18 | H | $CH_3$ | $NHC_2H_5$ | $CH_3$ | |
| 19 | Ca | $CH_3$ | $NHC_2H_5$ | H | |
| 20 | $C_2H_5$ | $CH_3$ | $NHC_6H_{13}$ | H | |
| 21 | $C_2H_5$ | H | $NH(CH_2)_2N(C_2H_5)_2$ | H | |

What is claimed is:

1. A compound of the formula

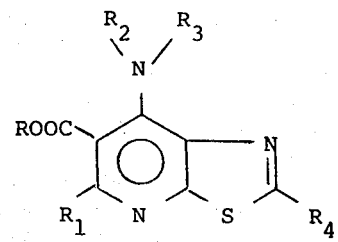

wherein R, $R_1$ and $R_4$ each is hydrogen or lower alkyl, and $R_2$ and $R_3$ each is hydrogen, lower alkyl, phenyl or di(lower alkyl)amino-lower alkyl, and physiologically acceptable salts thereof.

2. A compound as in claim 1 wherein R, $R_1$, $R_2$, $R_3$ and $R_4$ each is hydrogen or lower alkyl.

3. A compound as in claim 1 wherein R, $R_1$ and $R_4$ each is hydrogen or lower alkyl, $R_2$ is hydrogen and $R_3$ is di(lower alkyl)amino-lower alkyl.

4. A compound as in claim 1 wherein R, $R_1$ and $R_2$ each is lower alkyl and $R_3$ and $R_4$ each is hydrogen.

5. A compound as in claim 1 wherein R is ethyl, $R_1$ is methyl, $R_2$ is hydrogen, $R_3$ is butyl and $R_4$ is hydrogen.

6. A compound as in claim 1 wherein R is ethyl, $R_1$ and $R_4$ each is methyl, $R_3$ is butyl and $R_2$ is hydrogen.

7. A compound as in claim 1 wherein R is ethyl, $R_1$ and $R_4$ each is methyl, $R_2$ is hydrogen and $R_3$ is dimethylaminopropyl.

8. A compound as in claim 1 wherein R is ethyl, $R_1$ is methyl, $R_2$ and $R_4$ each is hydrogen and $R_3$ is dimethylaminopropyl.

9. A compound as in claim 1 wherein R is ethyl, $R_1$ is methyl, $R_2$ and $R_4$ each is hydrogen and $R_3$ is tert.butyl.

* * * * *